United States Patent

Drummey et al.

[11] Patent Number: 5,904,677
[45] Date of Patent: May 18, 1999

[54] STERILE SPECIMEN CAPTURE DEVICE

[76] Inventors: Thomas Hartnett Drummey; Patricia Maureen Drummey, both of 2 Warren Street, Plainville, Mass. 02762

[21] Appl. No.: 08/501,815

[22] Filed: Jul. 13, 1995

[51] Int. Cl.[6] .................................................. A61M 5/00
[52] U.S. Cl. ......................... 604/415; 604/403; 215/247
[58] Field of Search ................................ 128/760, 764, 128/767; 604/317, 406, 415, 403; 215/227, 235, 247, 249, 329

[56] References Cited

U.S. PATENT DOCUMENTS

| | | | |
|---|---|---|---|
| 2,142,278 | 1/1939 | Mendelson | 215/227 |
| 2,364,126 | 12/1944 | Cantor et al. | 215/247 |
| 2,585,938 | 2/1952 | Jordan | 604/406 |
| 2,608,972 | 9/1952 | Chrigstrom | 604/415 |
| 3,855,997 | 12/1974 | Sauer | 128/760 |
| 3,881,465 | 5/1975 | Raitto | 128/760 |
| 4,244,920 | 1/1981 | Manschot et al. | 604/317 X |
| 4,278,437 | 7/1981 | Haggar | 128/764 X |
| 4,863,453 | 9/1989 | Berger et al. | 604/415 |
| 5,139,492 | 8/1992 | Leise, Jr. et al. | 604/339 |
| 5,257,984 | 11/1993 | Kelley | 128/764 X |
| 5,297,561 | 3/1994 | Hulon | 128/764 |
| 5,384,096 | 1/1995 | Burns | 128/767 X |
| 5,458,854 | 10/1995 | Burns | 128/767 X |
| 5,611,792 | 3/1997 | Gustafsson | 604/403 |

FOREIGN PATENT DOCUMENTS

WO 94/18891  9/1994  WIPO .................................. 128/760

Primary Examiner—Richard J. Apley
Assistant Examiner—Benjamin K Koo
Attorney, Agent, or Firm—Brian M. Dingman

[57] ABSTRACT

A sterile specimen cup with a self-sealing membrane in the top that allows fluids to be injected into or with drawn from the cup with a syringe. This allows the specimen cup to be fully operated with one hand without removing the cover, thus increasing user safety, and sterility.

1 Claim, 2 Drawing Sheets

STERILE SPECIMEN CAPTURE DEVICE

FIELD OF THE INVENTION

This invention relates to a sterile specimen cup with a self-sealing membrane that allows specimens to be injected into the cup without removing the cover.

BACKGROUND OF THE INVENTION

At present, to use a specimen cup, the user must use both hands to operate the device. The user must hold the cup in one hand and remove the cover with the other, often while holding a needle and syringe containing an aspirated specimen. The user must then squirt the specimen into the open cup, risking the possibility of splash back or spillage.

SUMMARY OF THE INVENTION

This invention will allow the user to use a specimen cup with one hand. After aspirating a specimen from a wound or indwelling urine catheter, the user would hold the specimen cup of this invention in one hand, and flip open a cover with the thumb, to reveal a sterile self-sealing window that can be injected through. The user would then inject the specimen through the window, which virtually eliminates the danger of splash back. The user would then remove the needle and reseal the cover with the thumb.

It is therefore an object of the invention to obviate the deficiencies of the prior art.

It is a further object of this invention to add ease and safety to the user of a specimen cup.

It is a further object of this invention to decrease the chances of the spread of infectious disease.

It is a further object of this invention to provide a cleaner, more sterile catch of the specimen.

BRIEF DESCRIPTION OF THE DRAWINGS

Other objects, features and advantages will occur to those skilled in the art from the following description of the preferred embodiments, and the accompanying drawings, in which.

DESCRIPTION OF THE PREFERRED EMBODIMENT

Figure 1:
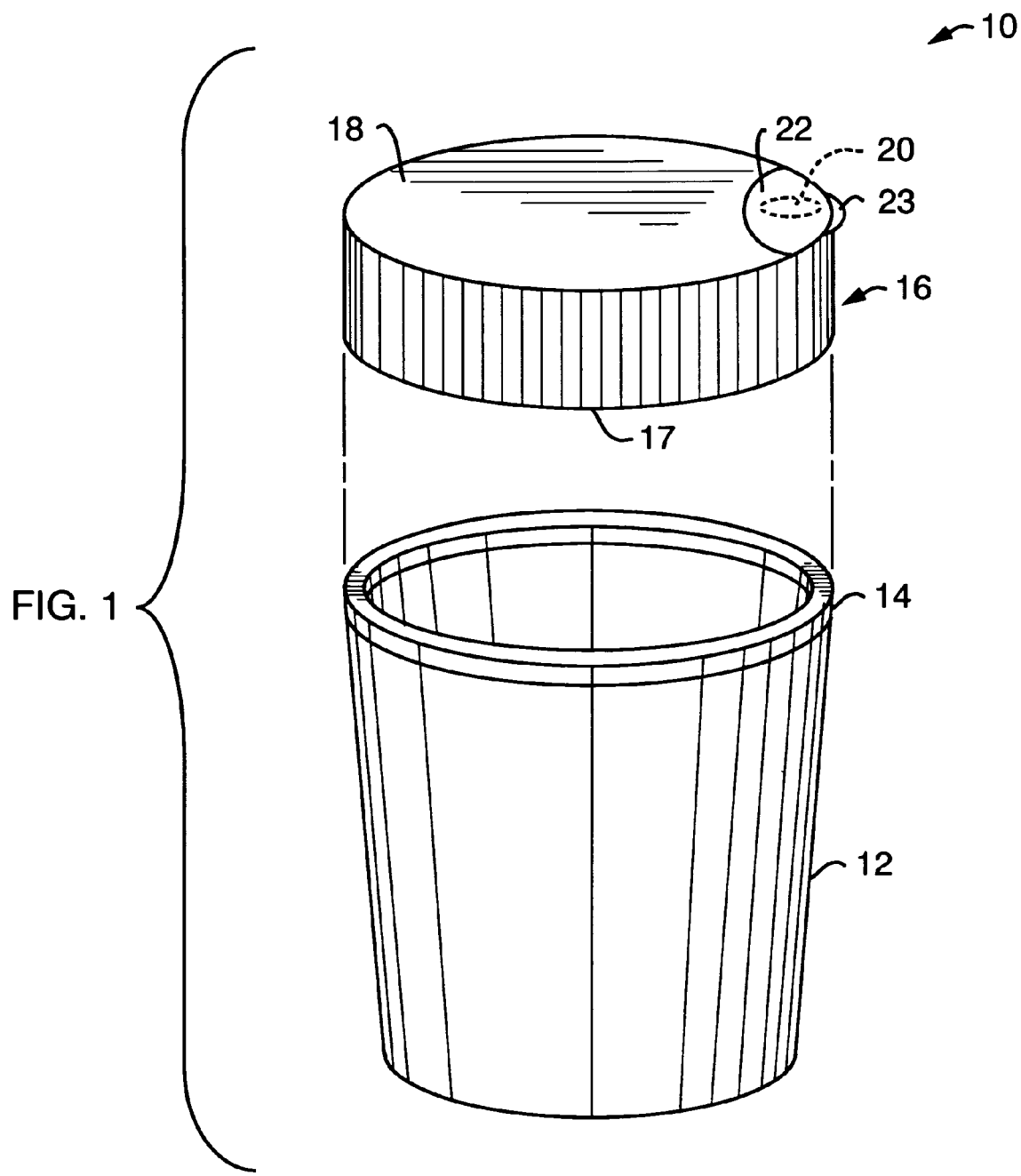
FIG. 1 is a disassembled front view of a preferred embodiment of the sterile specimen capture device of this invention.
Figure 2:
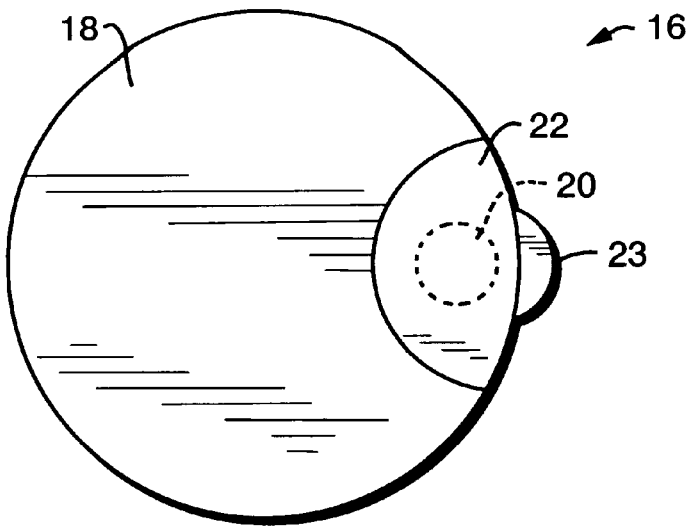
FIG. 2 is a top view of the top of the device of FIG. 1.
Figure 3:
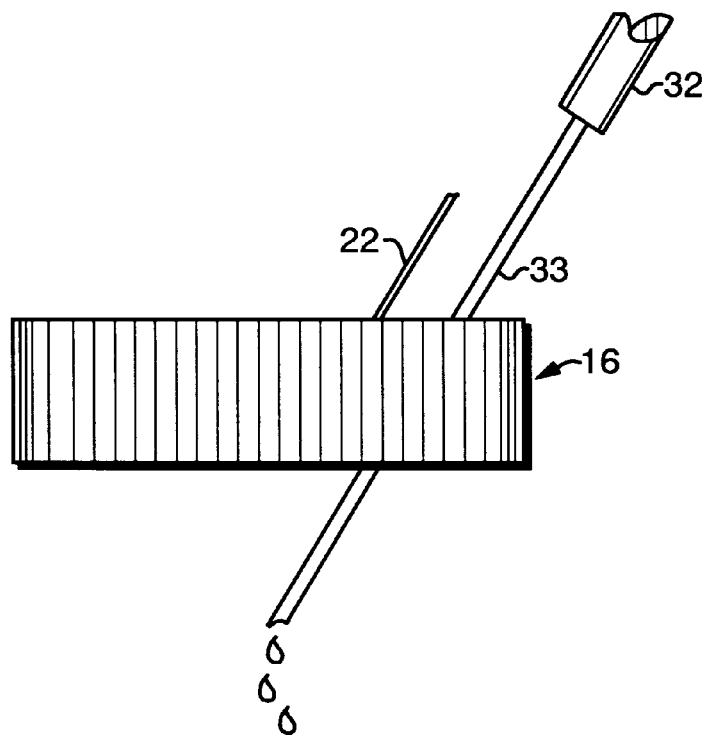
FIG. 3 is a side view of the top of FIG. 2 in use, with a specimen being injected into the device through the self-sealing window.

Sterile specimen capture device 10 according to this invention, is shown in figures one through three. Device 10 includes open-top specimen cup 12 with threaded top 14 that accepts the threaded inside of downwardly extending flange 17 of specimen cup lid 16 so that top 16 can be removed from cup 12. Top 16 has a flat circular top area 18 with an opening therethrough that is covered with self-sealing rubber membrane 20. Membrane 20 is of the type that will seal itself after being punctured with a hypodermic needle. Over cover 22 is hinged to top 18, to removably cover membrane 20. Over cover 22 includes tab portion 23 that extends beyond the periphery of lid 16, so that cover 22 can be lifted by upwardly-directed finger pressure. Over cover 22 is shown in its open position in FIG. 3, in which needle 33 of syringe 32 is shown piercing membrane 20.

Specimen cup 12 is a typical specimen cup, about two and one quarter inches in diameter at the top, and about three inches deep. The cup can hold up to about 4 ounces, and preferably has inscription on the side as a means of measurement. The cup and lid are preferably sterile. The self-sealing window is preferably about one inch in diameter.

Device 10 of this invention decreases the danger to the user of a specimen cup into which, or from which, a sample is injected or withdrawn, respectively. This is due to the fact that the device can be fully operated with only one hand, without the need to remove the cover. The user who has just aspirated a specimen from the wound or an indwelling urine catheter, and is holding the syringe in one hand, can pick up the device of this invention, flip open the over cover with the thumb to reveal the self-sealing window, inject the specimen through the window, withdraw the needle, and close the over cover with the thumb or a finger. There is thus less risk of accidental stabbing with the needle, or contact with the fluid.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A specimen capture device, comprising:

an open top specimen cup with external threads on its outer, upper surface;

an internally threaded specimen cup lid, having a center, adapted to be threadably received on the specimen cup threads, to removably cover the cup opening, the lid having a top covering the cup opening when the lid is threadably engaged with the cup, the top defining a lid opening, positioned off-center;

a self-sealing membrane covering the lid opening, to allow a hypodermic needle to be passed into the cup through the membrane for injection of a specimen into, or withdrawal from, the specimen cup; the membrane re-sealing on withdrawal of the needle to keep the specimen cup closed; and an over cover hingedly fixed to the top of the lid, and removably covering the membrane, the over cover including a tab portion extending beyond the periphery of the lid, to allow the over cover to be lifted by upwardly-directed finger pressure and lowered by downwardly-directed finger pressure.

* * * * *